US012557747B2

(12) United States Patent

Kawamura

(10) Patent No.: US 12,557,747 B2
(45) Date of Patent: Feb. 24, 2026

(54) S-METHYLMETHIONINE-RICH *BRASSICA OLERACEA* PLANT

(71) Applicant: SAKATA SEED CORPORATION, Yokohama (JP)

(72) Inventor: Manabu Kawamura, Yokohama (JP)

(73) Assignee: SAKATA SEED CORPORATION, Yokohama (JP)

( * ) Notice: Subject to any disclaimer, the term of this patent is extended or adjusted under 35 U.S.C. 154(b) by 1299 days.

(21) Appl. No.: 17/258,020

(22) PCT Filed: Jul. 9, 2019

(86) PCT No.: PCT/JP2019/027167
§ 371 (c)(1),
(2) Date: Jan. 5, 2021

(87) PCT Pub. No.: WO2020/013190
PCT Pub. Date: Jan. 16, 2020

(65) Prior Publication Data
US 2021/0274732 A1 Sep. 9, 2021

(30) Foreign Application Priority Data
Jul. 10, 2018 (JP) ................................ 2018-131069

(51) Int. Cl.
| | |
|---|---|
| *A01H 6/20* | (2018.01) |
| *A01H 1/00* | (2006.01) |
| *A01H 5/10* | (2018.01) |
| *C07C 319/28* | (2006.01) |

(52) U.S. Cl.
CPC ............... *A01H 1/108* (2021.01); *A01H 5/10* (2013.01); *A01H 6/203* (2018.05); *C07C 319/28* (2013.01)

(58) Field of Classification Search
None
See application file for complete search history.

(56) References Cited

FOREIGN PATENT DOCUMENTS

| | | | | |
|---|---|---|---|---|
| JP | 2007089572 | A | * | 4/2007 |
| JP | 2007089572 | B2 | * | 12/2007 |

| | | | | | |
|---|---|---|---|---|---|
| JP | 2010227113 | A | | 10/2010 | |
| JP | 2011-95165 | A | | 5/2011 | |
| JP | 2011095165 | A | * | 5/2011 | |
| JP | 2013-143920 | A | | 7/2013 | |
| KR | 2011040277 | A | * | 4/2011 | ............. A23L 2/382 |
| KR | 20110040277 | A | * | 4/2011 | |

OTHER PUBLICATIONS

Larina et al. (News of Institutions of Higher Education, Food Technology, No. 1-3, 1990, pp. 99-101.*
Ueda et al., "Vitamins of broccoli, Site-wise analysis of C,S-methylmethionine and polyphenol content and their impact on cellular function", Nippon Shokuhin Kagaku Kogaku Kaishi, 2015, vol. 62, No. 5, pp. 242-249. English translation 9 pages.
Office Action for Corresponding Japanese Patent Application No. 2020-530204, Nov. 2, 2021, 10 pages.
Office Action for Corresponding Chinese Patent Application No. 201980045998.8, May 7, 2022, 10 pages.
Otsuki, Kozo; et al., "Analysis of Vitamin U in Food and Nutritional Effects of its Analogues, etc.", Achievement Report of Fiscal Year 1988, Scientific Reports of Kyoto Prefectural University (Natural science and living science), Nov. 1989, No. 40, Series B, with English translation (3 pages).
Ueda, Keiko; et al., "Site-by-site Analysis of the Content of Vitamin C, S-methylmethylmethionine, and Polyphenol in Broccoli and Its Effect on Cell Function", Research report No. 25, Fukuoka Industrial Technology Center, 2015, with English translation (4 pages).
ISA/JP, WIPO, "PCT International Search Report", mailed Sep. 17, 2019, which was issued in connection with PCT international application No. PCT/JP2019/027167 (2 pages).
Scherb et al, "Quantitation of S-Methylmethionine in Raw Vegetables and Green Malt by a Stable Isotope Dilution Assay Using LC-MS/ MS: Comparison with Dimethyl Sulfide Formation after Heat Treatment", J. Agric. Food Chem. 2009, vol. 57, pp. 9091-9096.
Scarth et al., "Modification of Brassica Oil Using Conventional and Transgenic Approaches", Crop Science, 2006, vol. 46, pp. 1225-1236.
Office Action for Corresponding Indian Patent Application No. 202117002312, Sep. 19, 2025, 7 pages.

* cited by examiner

*Primary Examiner* — Vinod Kumar
(74) *Attorney, Agent, or Firm* — Lucas & Mercanti, LLP

(57) ABSTRACT

This invention provides a *Brassica oleracea* plant with high S-methylmethionine content. This invention relates to a *Brassica oleracea* plant with higher S-methylmethionine content than that in a conventional *Brassica oleracea* plant. Specifically, this invention relates to a *Brassica oleracea* plant with the S-methylmethionine content of 48 mg/100 g fresh weight or more.

5 Claims, 2 Drawing Sheets

S-METHYLMETHIONINE-RICH *BRASSICA OLERACEA* PLANT

CROSS-REFERENCE TO RELATED APPLICATIONS

This application is a 371 of PCT/JP2019/027167, filed Jul. 9, 2019, which claims the benefit of Japanese Patent Application No. 2018-131069, filed Jul. 10, 2018.

TECHNICAL FIELD

The present invention relates to *Brassica oleracea* plants with higher content of S-methylmethionine than conventional *Brassica oleracea* plants and a method for producing the same.

BACKGROUND ART

Plants in the family Brassicaceae are plant species originating from the Middle East and the Mediterranean coast, and plants of the genus *Brassica* encompass very important agricultural crops. In particular, *Brassica oleracea* (*Brassica oleracea* L.) is a very important plant species including *B. oleracea* L. var. *capitata* (cabbage), *Brassica oleracea* L. var. *italica* (broccoli), *Brassica oleracea* L. var. *botrytis* (cauliflower), *B. oleracea* L. var. *gemmifera* (Brussels sprouts), *B. oleracea* L. var. *gongyloides* (kohlrabi), *B. oleracea* L. var. *acephala* (kale), and *B. oleracea* L. var. *alboglabra* (Chinese kale) and other species.

Among plants of the genus *Brassica* in the family Brassicaceae, consumption in Japan of broccoli has been expanding since the 1980s. Florets and stems of broccoli are used for food, as broccoli is rich in vitamin B, vitamin C, vitamin A, and dietary fibers. It is also rich in carotene and iron, and it contains substances such as sulforaphane, which is considered to have cancer prevention properties. Thus, broccoli is recognized as a vegetable with many health benefits.

S-methylmethionine is a sulfur-containing amino acid that is also sometimes referred to as vitamin U or "cabagin" since it was found in cabbage. It is an anti-digestive tumor factor and it is present in its free form in vegetables.

The S-methylmethionine content in vegetables has been examined. According to the results of analysis provided in a report, the S-methylmethionine content in vegetables of Umbelliferae, Solanaceae, and Liliaceae is 1 to 4 mg % based on fresh weight and the content in vegetables in the family Brassicaceae is 4 to 20 mg % based on fresh weight. Among vegetables in the family Brassicaceae, in particular, the S-methylmethionine content in watercress, Chinese cabbage, and cabbage is relatively low (2 to 4 mg %), and that in cauliflower, broccoli, kohlrabi, and field mustard is as high as 10 to 20 mg % (Non-Patent Literature 1). The content in green tea is 1 to 9 mg % based on dry weight.

According to a report on distribution of nutritional components in different parts of broccoli, florets contain a large quantity of S-methylmethionine, and it is larger than that in other parts, such as stems, lower parts of the main axis, rachis, leaves, and roots; i.e., 16.7 mg/100 g FW (Non-Patent Literature 2).

Patent Literature 1 discloses a method of introducing heterologous chromosomes into plants to increase the amount of amino acid and/or amino acid-associated substance in plants. While S-methylmethionine is a type of amino acid, Patent Literature 1 does not disclose plants in the family Brassicaceae with an increased content of S-methylmethionine.

CITATION LIST

Patent Literature

Patent Literature 1: JP 2013-143920 A

Non-Patent Literature

Non-Patent Literature 1: Achievement report of fiscal year 1988, Kozo Ohtsuki, the scientific reports of Kyoto Prefectural University (Natural science and living science) 40, 1989

Non-Patent Literature 2: "Analysis of vitamin C content, S-methylmethionine content, and polyphenol content in different parts of broccoli and influence on cell function," the fiscal year of 2015, Fukuoka Industrial Technology Center, Research report No. 25

SUMMARY OF INVENTION

Technical Problem

The present invention provides *Brassica oleracea* plants with high S-methylmethionine content.

Solution to Problem

The present inventor has conducted studies to provide *Brassica oleracea* plants with high S-methylmethionine content. This has led to the completion of the present invention.

(1) A *Brassica oleracea* plant comprising S-methylmethionine in a content of 48 mg/100 g fresh weight (FW) or more.

(2) A *Brassica oleracea* plant having a genetic trait causing an increased content of S-methylmethionine in a plant, the genetic trait being present in a broccoli, the representative seeds of which are deposited under Accession Number: FERM BP-22352, or in a progeny of the broccoli having a genetic trait causing an increased content of S-methylmethionine in a plant.

(3) The *Brassica oleracea* plant according to (1) or (2), which is selected from a group consisting of broccoli, cauliflower, Chinese kale, cabbage, Brussels sprouts, kohlrabi, kale, and a hybrid thereof.

(4) The *Brassica oleracea* plant according to (3), which is broccoli.

(5) A part of the *Brassica oleracea* plant according to any of (1) to (4).

(6) A seed of the *Brassica oleracea* plant according to any of (1) to (4).

(7) A method for producing a *Brassica oleracea* plant comprising a step of cross pollinating the *Brassica oleracea* plant according to any of (1) to (4) with another *Brassica oleracea* plant.

(8) The method according to (7), wherein the *Brassica oleracea* plant comprises S-methylmethionine in a content of 48 mg/100 g FW or more.

(9) The method according to (7) or (8), which further comprises a step of producing doubled haploids from the progeny plants obtained in the step of cross pollinating via anther culture or pollen culture.

(10) A *Brassica oleracea* plant, a seed of the plant, or a part of the plant, the plant being obtainable by a method for producing a *Brassica oleracea* plant comprising a step of cross pollinating the *Brassica oleracea* plant according to any of (1) to (4) with another *Brassica oleracea* plant.

(11) The *Brassica oleracea* plant, the seed of the plant, or the part of the plant according to (10), comprising S-methylmethionine in a content of 48 mg/100 g FW or more.

(12) A method for producing a *Brassica oleracea* plant comprising S-methylmethionine in a content of 48 mg/100 g FW or more comprising:

a step of cross pollinating *Brassica oleracea* plants;

a step of producing doubled haploids from a progeny plant obtained in the step of cross pollinating via anther culture or pollen culture; and a step of selecting a *Brassica oleracea* plant comprising S-methylmethionine in a content of 48 mg/100 g FW or more from among the doubled haploids produced by the step of producing doubled haploids.

(13) An S-methylmethionine-containing composition, comprising the *Brassica oleracea* plant according to any of (1) to (4), a part of the plant, or a processed product of the plant or the part.

(14) A method for producing S-methylmethionine comprising obtaining S-methylmethionine from the *Brassica oleracea* plant according to any of (1) to (4), a part of the plant, or a processed product of the plant or the part.

(15) Use of the *Brassica oleracea* plant according to any of (1) to (4), a seed of the plant, or a part of the plant, for producing a *Brassica oleracea* plant comprising S-methylmethionine in a content of 48 mg/100 g FW or more.

(16) A *Brassica oleracea* plant with higher S-methylmethionine content than in a conventional *Brassica oleracea* plant.

(17) A *Brassica oleracea* plant with high S-methylmethionine content represented by broccoli deposited under Accession Number: FERM BP-22352.

This description includes part or all of the content as disclosed in the description and/or drawings of Japanese Patent Application No. 2018-131069, which is a priority document of the present application.

Advantageous Effects of Invention

The present invention provides a *Brassica oleracea* plant with high S-methylmethionine content.

The *Brassica oleracea* plant according to the present invention may be subjected to crosspollinting with another *Brassica oleracea* plant to produce a *Brassica oleracea* plant with high S-methylmethionine content.

The S-methylmethionine-containing composition of the present invention is useful for applications such as a pharmaceutical composition or food or beverage composition.

According to the method for producing S-methylmethionine of the present invention, naturally-occurring S-methylmethionine can be produced.

DESCRIPTION OF EMBODIMENTS

<*Brassica oleracea* Plants>

Figure 1:
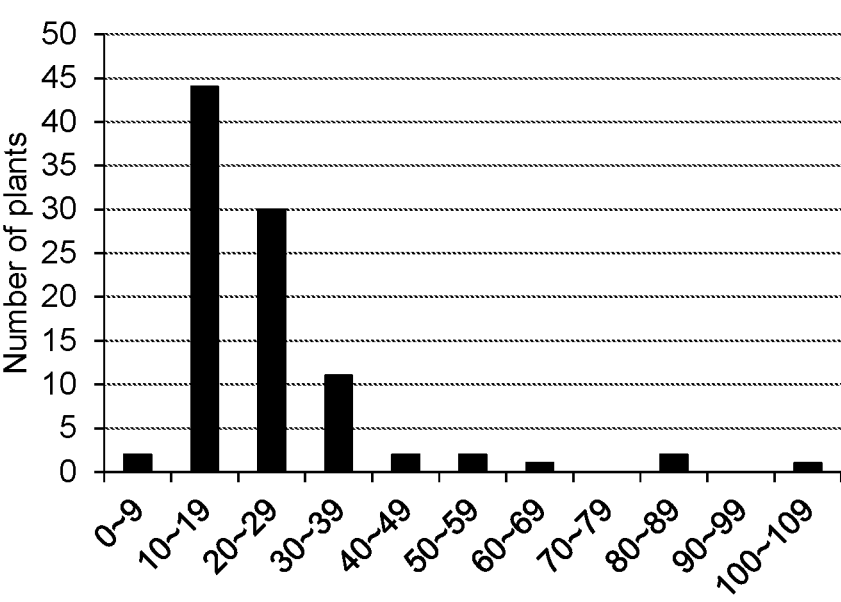
FIG. 1 shows a chart demonstrating the correlation between the S-methylmethionine content and the number of plants among the 95 F2 progeny plants derived from a hybrid resulting from crossing the line 4-1 (SSC-BRO-17-002) having high S-methylmethionine content with another line.

*Brassica oleracea* (*Brassica oleracea* L.) belonging to the family Brassicaceae encompass plants classified as broccoli, cauliflower, Chinese kale, cabbage, Brussels sprouts, kohlrabi, kale, plants that can be crosspollinated with any of such plants, and hybrid plants resulting from crosspollinating of such plants. The term "*Brassica oleracea* plants" refers to plants that belong to the aforementioned species.

In the present invention, broccoli includes *Brassica oleracea* plants belonging to *Brassica oleracea* L. var. *italica* and progenies thereof. In the present invention, the "progenies" of *Brassica oleracea* plants include the *Brassica oleracea* plants according to the present invention with high S-methylmethionine content and plants obtained via crosspollinating between the *Brassica oleracea* plants according to the present invention and other *Brassica oleracea* plants that can crosspollinate therewith. For example, hybrid species that can be obtained via crosspollinating between broccoli plants with high S-methyomethionine content according to the present invention and other *Brassica oleracea* plants that can crosspollinate therewith are within the scope of the "progenies" of broccoli. Also, plants obtained via cell fusion of the *Brassica oleracea* plants with high S-methylmethionine content according to the present invention and other *Brassica oleracea* plants that can be cell-fused therewith, interspecific hybrid plants, and the like are within the scope of "progenies."

In the present invention, a method for quantification of S-methylmethionine is not particularly limited, provided that the S-methylmethionine content in a plant can be determined with reproducibility. Examples of methods that can be employed include a method of quantification via amino acid fluorescent labeling of a plant extract in HPLC, a method of indirect quantification via gas chromatography, an analytical method comprising directly injecting a plant extract into a lithium-based amino acid analyzer and directly separating and quantifying S-methylmethionine, and a method of re-suspending a precipitate extracted from a dried plant sample in a buffer and performing analysis using an amino acid analyzer.

In the present invention, for example, a broccoli sample for quantification of S-methylmethionine content is obtained at the time of broccoli harvesting. Specifically, the broccoli sample is obtained when the head, also referred to as the flower bud inflorescence, diameter reaches its average size; i.e., 10 to 15 cm. The primary harvested portion of broccoli, commonly referred to as the head, is a compound inflorescence, or synflorescence, possessing a terminal florescence and multiple lateral florescences, commonly referred to as florets.

The first aspect of the present invention relates to *Brassica oleracea* plants with higher content of S-methylmethionine than in conventional *Brassica oleracea* plants. When S-methylmethionine content in plants is higher than that in conventional *Brassica oleracea* plants, the S-methylmethionine content per unit weight of the plants is higher than that in conventional *Brassica oleracea* plants. While plant parts to be subjected to assays and comparison of the S-methylmethionine content are not particularly limited, florets, stems, or leaves are preferable, florets or stems are more preferable, and florets are particularly preferable.

A specific example of *Brassica oleracea* plants with higher content of S-methylmethionine than in conventional *Brassica oleracea* plants is preferably *Brassica oleracea* plants comprising S-methylmethionine in a content of 48 mg/100 g FW or more. The S-methylmethionine content is preferably assayed at the time of harvesting. In the case of broccoli, the S-methylmethionine content is more preferably assayed when the head diameter reaches 10 to 15 cm. In the case of stick broccoli (also known as baby broccoli), the S-methylmethionine content is preferably assayed when the head diameter reaches 3 to 4 cm. The S-methylmethionine content is preferably the S-methylmethionine content in florets, stems, or leaves, more preferably the S-methylme-thionine content in florets or stems, and particularly prefer-ably the S-methylmethionine content in florets. When *Bras-sica oleracea* plants are broccoli, in particular, the S-methylmethionine content is 48 mg/100 g FW or more preferably in florets, stems, or leaves at the time of harvest-ing, more preferably in florets or stems at the time of harvesting, and particularly preferably in florets at the time of harvesting.

The S-methylmethionine content in the *Brassica oleracea* plants of the present invention is more preferably 50 mg/100 g FW or more, 55 mg/100 g FW or more, 60 mg/100 g FW or more, 65 mg/100 g FW or more, or 70 mg/100 g FW or more. The S-methylmethionine content in the *Brassica oleracea* plants of the present invention is generally 200 mg/100 g FW or less, such as 150 mg/100 g FW or less or 130 mg/100 g FW or less.

The *Brassica oleracea* plants of the present invention are more preferably *Brassica oleracea* plants having a trait of high S-methylmethionine content represented by a broccoli, the seeds of which are internationally deposited under Accession Number FERM BP-22352 (broccoli line: SSC-BRO-17-002), or progenies thereof, particularly preferably *Brassica oleracea* plants having a trait of high S-methyl-methionine content represented by the broccoli, the seeds of which are internationally deposited under Accession Num-ber FERM BP-22352, and most preferably the broccoli, the seeds of which are internationally deposited under Acces-sion Number FERM BP-22352, or progenies thereof. In this broccoli line, the S-methylmethionine content is particularly high.

One or more other preferable embodiments of the *Bras-sica oleracea* plant according to the present invention are related to a *Brassica oleracea* plant having a genetic trait causing an increased content of S-methylmethionine in a plant, the genetic trait being present in the broccoli, the representative seeds of which are deposited under Accession Number: FERM BP-22352, or in a progeny of the broccoli having a genetic trait causing an increased content of S-methylmethionine in a plant. The embodiments described below confirmed that the genetic trait of the broccoli, the representative seeds of which are deposited under Accession Number FERM BP-22352, causing an increased content of S-methylmethionine in plants, is an inheritable genetic trait.

The term "a genetic trait causing an increased content of S-methylmethionine in a plant" used herein refers to a genetic trait such that the S-methylmethionine content in plants, preferably in florets, stems, or leaves, more prefer-ably in florets or stems, and particularly preferably in florets is preferably 48 mg/100 g FW or more, 50 mg/100 g FW or more, 55 mg/100 g FW or more, 60 mg/100 g FW or more, 65 mg/100 g FW or more, or 70 mg/100 g FW or more to more preferably 200 mg/100 g FW or less, such as 150 mg/100 g FW or less or 130 mg/100 g FW or less.

When the *Brassica oleracea* plants according to the embodiment of the present invention have a genetic trait causing an increased content of S-methylmethionine in a plant and the genetic trait is "present" in a broccoli, the representative seeds of which are deposited under Accession Number: FERM BP-22352, or in a progeny of the broccoli having the genetic trait causing an increased content of S-methylmethionine in a plant, the genetic trait is the same (or substantially the same) as the genetic trait causing an increased content of S-methylmethionine in plants of the broccoli or the progenies thereof. More preferably, the genetic trait causing an increased content of S-methylme-thionine in the *Brassica oleracea* plants according to the embodiment of the present invention can be derived from the broccoli, the representative seeds of which are deposited under Accession Number FERM BP-22352, or from the progenies of the broccoli having a genetic trait causing an increased content of S-methylmethionine in plants. A person skilled in the art would readily transfer the genetic trait causing an increased content of S-methylmethionine in plants of the broccoli, the representative seeds of which are deposited under Accession Number FERM BP-22352, or the progenies thereof having the genetic trait to other plants by using adequate techniques without undue trials and errors.

The second aspect of the present invention relates to parts of the *Brassica oleracea* plants according to the present invention. Examples of parts of the *Brassica oleracea* plants according to the present invention include florets, leaves, stems, roots, flowers, cells, and nucleic acids, with florets, stems, or leaves being preferable, florets or stems being more preferable, and florets being particularly preferable. Alternatively, a mixture of a plurality of parts may be used.

The third aspect of the present invention relates to seeds of the *Brassica oleracea* plants according to the present invention. Examples of seeds include the seeds of the broccoli line: SSC-BRO-17-002, which are internationally deposited under Accession Number FERM BP-22352.

<A Method for Producing *Brassica oleracea* Plants with High S-Methylmethionine Content 1>

The fourth aspect of the present invention relates to a method for producing *Brassica oleracea* plants comprising a step of crossing the *Brassica oleracea* plants according to the present invention with other *Brassica oleracea* plants.

The other *Brassica oleracea* plants are not particularly limited, provided that such plants can produce progeny seeds as a result of the crossing with the *Brassica oleracea* plants according to the present invention.

In the *Brassica oleracea* plants produced in the method, the S-methylmethionine content is preferably increased from that in the other parent *Brassica oleracea* plants. It is particularly preferable that *Brassica oleracea* plants pro-duced in the method comprises S-methylmethionine in a content of 48 mg/100 g FW or more. A more preferable range of the S-methylmethionine content in the plants is as described above with regard to the *Brassica oleracea* plants according to the present invention.

The method may further comprise a step of selecting plants with high S-methylmethionine content from among the plants obtained in the crossing step. A method for quantification of S-methylmethionine in plants for selection is as described above with regard to the *Brassica oleracea* plants according to the present invention.

The method for producing *Brassica oleracea* plants with high S-methylmethionine content according to the present invention more preferably comprises, in addition to the step of crossing, a step of producing doubled haploids from the progeny plants obtained in the step of crossing via anther culture or pollen culture. Doubled haploids can be produced via anther culture or pollen culture in accordance with a conventional technique. For example, doubled haploids can be produced in accordance with Palmer, C. E. et al., 1996, "In Vitro Haploid Production in Higher plants," Vol. 3, Kluwer Academic Publishers, (ed.): Jain, S. M., Sopory, S. K., and Veilleux, R. E., pp. 143 to 172.

<A Method for Producing *Brassica oleracea* Plants with High S-Methylmethionine Content 2>

The fifth aspect of the present invention relates to a method for producing *Brassica oleracea* plants comprising S-methylmethionine in a content of 48 mg/100 g FW or more comprising:

a step of cross pollinating of *Brassica oleracea* plants;

a step of producing doubled haploids from the progeny plants obtained in the step of cross pollinating via anther culture or pollen culture; and a step of selecting *Brassica oleracea* plants comprising S-methylmethionine in a content of 48 mg/100 g FW or more from among the doubled haploids produced by the step of producing doubled haploids.

In Example 4, a plurality of recessive factors is deduced to be associated with the capacity for producing S-methylmethionine in *Brassica oleracea* plants. Accordingly, it is considered very difficult to produce *Brassica oleracea* plants comprising S-methylmethionine in a content of 48 mg/100 g FW or more by a conventional breeding method comprising repeated crossing and selection. According to the method of the present aspect comprising the step of crossing, the step of producing doubled haploids, and the step of selection, *Brassica oleracea* plants comprising S-methylmethionine in a content of 48 mg/100 g FW or more can be efficiently produced.

The step of producing doubled haploids can be performed in accordance with the procedure described in the literature described above or the like.

Specific examples of the *Brassica oleracea* plants are as described with regard to the *Brassica oleracea* plants according to the present invention.

The preferable range of S-methylmethionine content and other properties of the *Brassica oleracea* plants produced by the method are as described with regard to the *Brassica oleracea* plants according to the present invention.

A method for quantification of S-methylmethionine in plants for selection is as described with regard to the *Brassica oleracea* plants according to the present invention.

<S-Methylmethionine-Containing Composition>

The sixth aspect of the present invention relates to an S-methylmethionine-containing composition, which comprises the *Brassica oleracea* plants according to the present invention, parts thereof, or processed products of the plants or the parts.

The S-methylmethionine-containing composition is preferably an ingestible composition, such as a pharmaceutical composition or a food or beverage composition.

The *Brassica oleracea* plants or parts thereof according to the present invention are as described above.

Examples of the processed products of the plants or parts thereof include products resulting from at least one treatment of the plants or parts thereof selected from among dehydration, grinding, extraction, and squeezing. Products resulting from two or more types of treatments are also within the scope of the processed products of the plants or parts.

The S-methylmethionine-containing composition can contain other components, in addition to the plants, parts thereof, or processed products of the plants or the parts thereof. Examples of the other components include excipients, carriers, and solvents (e.g., water) that are acceptable for oral ingestion applications, such as pharmaceutical and food or beverage products.

<Method for Producing S-Methylmethionine>

The seventh aspect of the present invention relates to a method for producing S-methylmethionine comprising obtaining S-methylmethionine from the *Brassica oleracea* plants of the present invention, parts thereof, or the processed products of the plants or parts thereof.

Specific examples of the plants, the parts thereof, and the processed products are as described above.

In "obtaining S-methylmethionine," it is not limited to a case of obtaining S-methylmethionine as an isolated component, and it generally encompasses obtaining relatively high-concentrated S-methylmethionine from the plants, the parts thereof, or the processed products thereof. Specifically, S-methylmethionine may be in the form of a crudely purified product.

S-methylmethionine can be obtained from the plants, the parts thereof, or the processed products thereof by any procedure, such as column chromatography or solvent extraction, and the procedure is not limited thereto.

The resulting S-methylmethionine can be used in end applications, such as a pharmaceutical composition or a food or beverage composition.

EXAMPLES

The present invention is described in greater detail with reference to the following examples and comparative examples, although these examples are not intended to limit the scope of the present invention.

<Cultivation Method: Method of Sampling from Plants>

After sowing seeds, seedlings grown suitable for transplanting in cell trays were transplanted in the field, the seedlings were cultivated under common management practices, were harvested when their curds are at the proper time for harvesting, and the harvested florets were stored in a freezer.

<Quantification Method: Method of Quantification of S-Methylmethionine>

The plant samples were homogenized using 2% phosphoric acid. The homogenate was centrifuged at 3,000 rpm for 10 minutes, and the supernatant was collected as an S-methylmethionine extract. S-methylmethionine contained in the supernatant was subjected to a reaction with an amino acid and drug fluorescent labeling reagent (NBD-F: 4-fluoro-7-nitrobenzofurazan) at 60° C. for 5 minutes to prepare a fluorescent derivative, and the resultant was designated as an assay sample. The assay sample was analyzed via HPLC (LC10-ADvp, manufactured by Shimadzu Corporation) equipped with ODS columns (Shiseido Co., Ltd.) and a fluorescent detector to quantify S-methylmethionine.

The amount of S-methylmethionine is indicated in terms of the weight (mg) of S-methylmethionine based on 100 g fresh weight of the assay part (florets, stems, or leaves).

Comparative Example 1

In Spring 2006, 30 existing parent lines and first-filial (F1) hybrid varieties of broccoli were cultivated, and florets thereof were harvested, followed by sampling. Table 1 shows the results of quantification of S-methylmethionine. As a result of extensive analysis, the florets of the line H of the present invention were found to contain S-methylmethionine at 32.8 mg/100 g FW, which was the highest content.

TABLE 1

| Variety | Provider | Assay site | S-methylmethionine (mg/100 g FW) |
|---|---|---|---|
| Green Magic | Sakata Seed Corporation | Florets | 10.2 |
| Green Magic | Sakata Seed Corporation | Leaves | 0.5 |
| Gypsy | Sakata Seed Corporation | Florets | 10.9 |
| Green Belt | Sakata Seed Corporation | Florets | 8.7 |
| Patron | Sakata Seed Corporation | Florets | 9.9 |
| Marathon | Sakata Seed Corporation | Florets | 6.4 |
| Maximo | Sakata Seed Corporation | Florets | 9.9 |
| K3-081 | Sakata Seed Corporation | Florets | 14.1 |
| K3-084 | Sakata Seed Corporation | Florets | 7.2 |
| K4-087 | Sakata Seed Corporation | Florets | 6.8 |
| SK0-070 | Sakata Seed Corporation | Florets | 10.6 |
| SK0-070 | Sakata Seed Corporation | Leaves | 0.8 |
| Sachiyoshi | Mikado Kyowa Seed Co., Ltd. | Florets | 10.0 |
| Takamori | Mikado Kyowa Seed Co., Ltd. | Florets | 13.9 |
| Forest | Takii & Co., Ltd. | Florets | 8.5 |
| Subaru | Brolead Co., Ltd. | Florets | 10.0 |
| Middle-early green port | Marutane Co., Ltd. | Florets | 11.4 |
| North bell | Watanabe Noji Co., Ltd. | Florets | 14.6 |
| Salinas early | The Musashino Seed Co., Ltd. | Florets | 16.8 |
| OASIS807F1 | Agriseeds | Florets | 9.0 |
| Florette | Asgrow | Florets | 17.8 |
| Line A | Sakata Seed Corporation | Florets | 12.2 |
| Line B | Sakata Seed Corporation | Florets | 20.9 |
| Line C | Sakata Seed Corporation | Florets | 5.6 |
| Line D | Sakata Seed Corporation | Florets | 11.6 |
| Line E | Sakata Seed Corporation | Florets | 10.9 |
| Line 1 | Sakata Seed Corporation | Florets | 7.9 |
| Line F | Sakata Seed Corporation | Florets | 12.6 |
| Line G | Sakata Seed Corporation | Florets | 28.5 |
| Line H | Sakata Seed Corporation | Florets | 32.8 |

Example 1

The present inventor obtained a broccoli line 4-1 (SSC-BRO-17-002) from among a doubled haploid line obtained via anther culture from progenies resulting from crossing the hybrid progenies of the broccoli line 1 and the broccoli line 2 with the broccoli line 3.

Surprisingly, the present inventor found properties, such that the S-methylmethionine content would be significantly high in SSC-BRO-17-002 and in a novel F1 variety obtained by crossing SSC-BRO-17-002 with another broccoli line 5 (see Examples 2 and 3).

The seeds of the broccoli line SSC-BRO-17-002 are deposited internationally at the Patent Microorganisms Depositary, the National Institute of Technology and Evaluation (#120, 2-5-8 Kazusakamatari, Kisarazu-shi, Chiba, 292-0818, Japan) as of Dec. 15, 2017 (identification by the depositor: SSC-BRO-17-002; Accession Number: FERM BP-22352).

Example 2

In order to determine a fluctuation in the S-methylmethionine content in broccoli plants, 4 broccoli varieties sown and transplanted in August to September, 2012 in Field 1 or Field 2 were analyzed in terms of the S-methylmethionine content to observe a seasonal fluctuation. The results are shown in Table 2. Florets were subjected to assays. The novel F1 hybrid variety described in Example 1 was found to have a very high S-methylmethionine content in comparison with existing other broccoli varieties.

TABLE 2

| Variety | Cultivation site | Sowing date | Sampling date | S-methylmethionine (mg/100 g FW) |
|---|---|---|---|---|
| Pixel | Field 1 | August 1 | October 24 | 17 |
| (Sakata Seed | | August 1 | October 25 | 13 |
| Corporation) | | August 10 | November 8 | 21 |
| | | August 20 | January 7 | 30 |
| Ohayou | Field 1 | August 1 | October 22 | 17 |
| (Sakata Seed | | August 1 | October 24 | 17 |
| Corporation) | | August 10 | October 31 | 18 |
| | | August 20 | January 17 | 18 |
| | | August 30 | February 5 | 12 |
| Grandome | Field 1 | August 1 | November 28 | 15 |
| (Sakata Seed | | August 1 | November 28 | 21 |
| Corporation) | | August 10 | December 13 | 26 |
| | | August 20 | February 5 | 2 |
| | | August 30 | February 21 | 14 |
| | | September 10 | February 28 | 7 |
| | | September 20 | March 15 | 17 |
| | Field 2 | August 6 | November 15 | 40 |
| | | August 20 | January 8 | 38 |

TABLE 2-continued

| Variety | Cultivation site | Sowing date | Sampling date | S-methylmethionine (mg/100 g FW) |
|---|---|---|---|---|
| Novel F1 variety | Field 1 | August 1 | November 8 | 63 |
| | | August 1 | November 8 | 49 |
| | | August 10 | November 20 | 72 |
| | | August 20 | February 5 | 87 |
| | | August 30 | February 21 | 54 |
| | Field 2 | August 5 | November 7 | 82 |
| | | August 20 | January 8 | 123 |

Example 3

The broccoli lines shown in Table 3 were cultivated in Field 1 in 2015, and the S-methylmethionine content in florets was assayed. Assays were carried out using florets harvested from 3 plants of each line, and the averages thereof were determined. The results are shown in Table 3.

The line 5 and SSC-BRO-17-002 are as described in Example 1, and the line G is as described in Comparative Example 1.

As described in Example 1, the line 4-1 (SSC-BRO-17-002) and the lines 4-2, 4-3, 4-4, 4-5, and 4-6 shown in Table 3 were obtained from doubled haploid lines obtained via anther culture from progenies resulting from crossing the hybrid progenies of the parent line 1 and the parent line 2 with the parent line 3.

The line 7 was selected from among hybrid progenies of the line 5 and the line 8.

As a result, the S-methylmethionine content was found to be 48 mg/100 g FW or more in the lines 4-1, 4-3, 4-5, and 4-6 and the line 7.

TABLE 3

| Line | Harvesting date | S-methylmethionine (mg/100 g FW) | | | |
|---|---|---|---|---|---|
| | | 1 | 2 | 3 | Average |
| Line 5 | December 27 | 36 | 31 | 40 | 36 |
| Line 1 | December 5 | 11 | 22 | 19 | 17 |
| Line J | January 11 to Febuary 21 | 40 | 9 | 4 | 18 |
| Line G | January 31 to Febuary 21 | 10 | 7 | 7 | 8 |
| Line 6 | December 27 | 9 | 14 | 13 | 12 |
| Line 4-1 (SSC-BRO-17-002) | December 5 to December 16 | 64 | 94 | 67 | 75 |
| Line K | January 19 to January 31 | 18 | 12 | 20 | 17 |
| Line L | January 31 | 34 | 29 | 25 | 29 |
| Line M | December 27 | 20 | 23 | 19 | 21 |
| Line N | December 20 to December 27 | 5 | 6 | 8 | 6 |
| Line Q | December 20 | 8 | 10 | 10 | 9 |
| Line P | December 20 | 7 | 9 | 12 | 9 |
| Line 7 | March 7 | 49 | 49 | 64 | 54 |
| Line 4-2 | December 9 | 28 | 41 | 53 | 41 |
| Line 4-3 | December 9 | 55 | 67 | 65 | 62 |
| Line 4-4 | December 20 | 5 | 4 | 7 | 5 |
| Line 4-5 | December 20 | 46 | 57 | 41 | 48 |
| Line 4-6 | January 11 | 46 | 55 | | 50 |

Example 4 (Hereditary Patterns)

Seeds of the broccoli line 4-1 (SSC-BRO-17-002) prepared in Example 1, the broccoli line 5 described in Example 1, the novel F1 variety described in Example 1 as an F1 hybrid of the line 4-1 and the line 5, another broccoli line 6, F1-2 as an F1 hybrid of the line 4-1 and the line 6, and F1-2-1 as an F2 progeny self-reproduced from the F1-2 were produced and sown to investigate the hereditary patterns of the S-methylmethionine content. The 6 plants of the parent lines (line 4-1 (SSC-BRO-17-002), line 5, and line 6), the 9 plants of the F1 hybrid (novel F1 variety, F1-2), and the 95 F2 progeny plants (F1-2-1) were analyzed to confirm the distribution of the S-methylmethionine content in florets, and the averages were determined. The population of the F2 progeny plants (F1-2-1) exhibited the distribution shown in Table 1. Table 4 shows the average S-methylmethionine content of each line.

Figure 2:
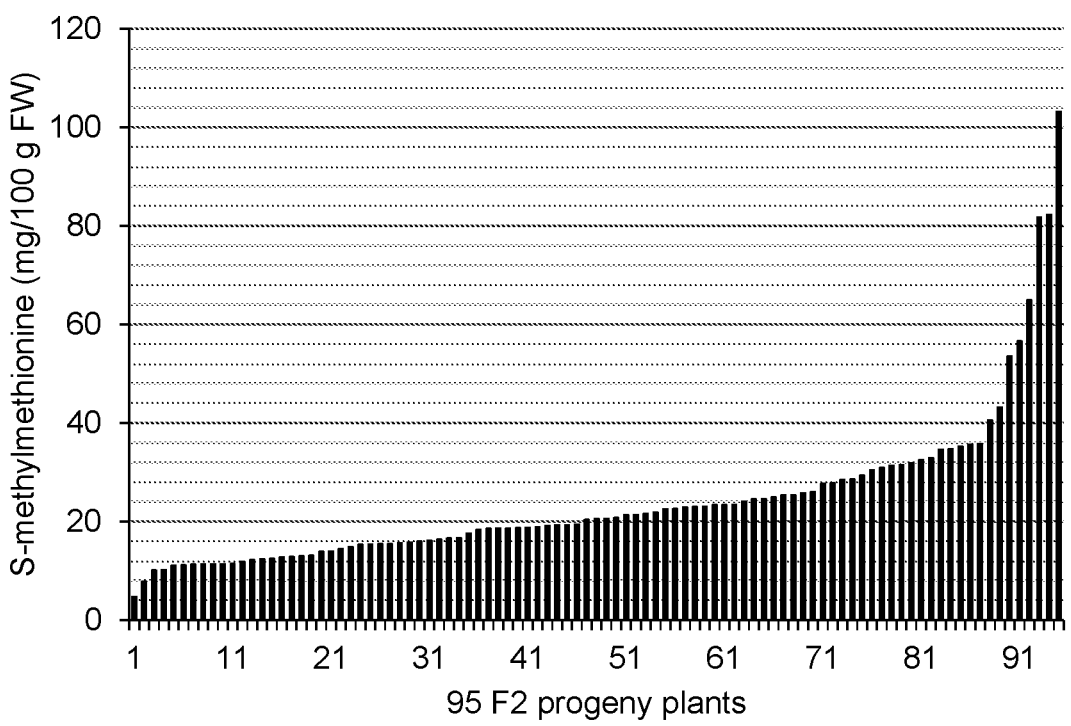
FIG. 2 shows a chart demonstrating the 95 F2 progeny plants derived from a hybrid resulting from crossing the line 4-1 (SSC-BRO-17-002) having high S-methylmethionine content with another line, in ascending order of the S-methylmethionine content.

As shown in FIG. 1, a majority of the 95 F2 progeny plants (F1-2-1) was found to have a low S-methylmethionine content and a low average (24 mg/100 g FW). FIG. 2 shows the results on the 95 F2 progeny plants (F1-2-1) in ascending order of the S-methylmethionine content. It shows a dispersed state from 5 mg/100 g FW at the minimum to 103 mg/100 g FW at the maximum. On the basis of the S-methylmethionine content of the F2 progeny plants of the line 4-1 and the line 6 independently assayed, a plurality of recessive factors is deduced to be associated, although the details remain unknown.

TABLE 4

| Line | S-methylmethionine (mg/100 g FW) |
|---|---|
| Line 5 | 37 |
| Line 4-1 (SSC-BRO-17-002) | 85 |
| Novel F1 variety | 51 |
| Line 6 | 15 |
| F1-2 | 20 |
| F1-2-1 | 24 |

All publications, patents, and patent applications cited herein are incorporated herein by reference in their entirety.

The invention claimed is:

1. A double haploid plant of broccoli (*Brassica oleracea* L. var. *italica*) line designated SSC-BRO-17-002, wherein said broccoli line comprises a heritable genetic trait characterized by S-methylmethionine content of at least 64 mg/100 g fresh weight (FW) and not more than 94 mg/100 g fresh weight (FW) in florets, and wherein representative seed of said broccoli line having been deposited under Accession No: FERM BP-223522.

2. A plant part or a plant progeny of the double haploid plant of broccoli (*Brassica oleracea* L. var. *italica*) line SSC-BRO-17-002 according to claim 1, wherein said plant part and said plant progeny comprises said florets, and wherein said florets comprise said heritable genetic trait characterized by having at least 64 mg/100 g fresh weight (FW) and not more than 94 mg/100 g fresh weight (FW) of S-methylmethionine content in said florets.

3. A seed that produces the double haploid plant of broccoli (*Brassica oleracea* L. var. *italica*) line SSC-BRO-17-002 according to claim 1, wherein said seed comprises the heritable genetic trait characterized by having at least 64 mg per 100 g FW and not more than 94 mg per 100 g FW of S-methylmethionine content in the florets of said broccoli plant line produced from said seed.

4. An F1 hybrid broccoli (*Brassica oleracea* L. var. *italica*) plant produced by crossing the double haploid plant of broccoli (*Brassica oleracea* L. var. *italica*) line SSC-BRO-17-002 according to claim 1 with another plant of broccoli (*Brassica oleracea* L. var. *italica*) line, wherein the F1 hybrid (*Brassica oleracea* L. var. *italica*) plant comprises said heritable genetic trait characterized by having at least 64 mg/100 g fresh weight (FW) and not more than 94 mg/100 g fresh weight (FW) of S-methylmethionine content in its florets.

5. A method for producing a broccoli (*Brassica oleracea* L. var. *italica*) plant comprising a heritable genetic trait characterized by having at least 64 mg/100 g fresh weight (FW) and not more than 94 mg/100 g fresh weight (FW) of S-methylmethionine content in florets, the method comprises the steps of:

(a) crossing the double haploid plant of broccoli (*Brassica oleracea* L. var. *italica*) line SSC-BRO-17-002 according to claim 1 with another plant of broccoli (*Brassica oleracea* L. var. *italica*) line;

(b) obtaining F1 hybrid broccoli (*Brassica oleracea* L. var. *italica*) plant from the cross of step (a);

(c) producing double haploid broccoli plants from F1 hybrid broccoli (*Brassica oleracea* L. var. *italica*) plant from step (b); and (d) selecting a double haploid broccoli (*Brassica oleracea* L. var. *italica*) plant from step (c), wherein the selected double haploid broccoli (*Brassica oleracea* L. var. *italica*) plant comprises said heritable genetic trait characterized by having at least 64 mg/100 g fresh weight (FW) and not more than 94 mg/100 g fresh weight (FW) of S-methylmethionine content in florets.

* * * * *